United States Patent
Rupaner et al.

(10) Patent No.: US 6,380,353 B1
(45) Date of Patent: Apr. 30, 2002

(54) METHOD FOR REDUCING THE $C_1$-$C_2$-ALDEHYDE CONTENT FORMED FROM COMPOUNDS WITH -$CH_2$-CHR-O-OR-CH(OH)-GROUPS

(75) Inventors: Robert Rupaner, Guaratingueta (BR); Martin Scholtissek, Mannheim (DE); Karl-Heinz Schumacher, Neustadt (DE); Maximilian Angel, Schifferstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/623,510

(22) PCT Filed: Mar. 31, 1999

(86) PCT No.: PCT/EP99/02216

§ 371 Date: Sep. 29, 2000

§ 102(e) Date: Sep. 29, 2000

(87) PCT Pub. No.: WO99/51647

PCT Pub. Date: Oct. 14, 1999

(30) Foreign Application Priority Data

Apr. 2, 1998 (DE) .......................... 198 14 873

(51) Int. Cl.⁷ ............................ C08F 6/56; C08G 65/30
(52) U.S. Cl. .................... 528/492; 528/480; 524/555; 524/801; 524/827
(58) Field of Search ................... 528/492, 480; 524/555, 801, 827

(56) References Cited

U.S. PATENT DOCUMENTS

| | | |
|---|---|---|
| 3,590,100 A | 6/1971 | Weiland |
| 3,957,431 A | 5/1976 | Pai et al. |
| 4,127,382 A | 11/1978 | Perry |
| 5,143,954 A | 9/1992 | Hutton et al. |
| 5,331,024 A | 7/1994 | Brink et al. |
| 5,453,485 A | 9/1995 | Huth et al. |

FOREIGN PATENT DOCUMENTS

| | | |
|---|---|---|
| EP | 0 080 635 | 6/1983 |
| EP | 0 143 175 | 6/1985 |
| EP | 341 569 | 11/1989 |
| EP | 488 605 | 9/1992 |
| EP | 527 411 | 2/1993 |
| EP | 492 378 | 7/1994 |
| EP | 0 647 658 | 4/1995 |
| EP | 0 661 305 | 7/1995 |
| EP | 505 959 | 9/1995 |
| GB | 2 086 929 | 5/1982 |

OTHER PUBLICATIONS

H. Kaczmarek, et al., Macromol. Symp. 84, pp. 351 to 363, "Oxidative Degradation of Water—Soluble Polyethers by HO and $HO_2$ Generated Photochemically: FT–IR Studies", 1994.

R. Janik, VI. Internationale Tagung Ueber Grenzflaechenaktive Stoffe, pp. 551 to 555, "Autoxidation Von Diethylen–UND Dipropylenglykolen UND Deren Methylethern", 1987.

H. Hidaka, et al., J. Jpn. Oil Chem. Soc. (Yukagaku), vol. 39, No. 11, pp. 963 to 966, "Photodegradation of Surfactants. VII. Peroxide and Aldehyde Formation in the Photocatalyzed Oxidation of Nonionic Surfactants", 1990.

H. Petersen, et al., Textile Research Journal, pp. 282 to 302, "Reagents for Low–Formaldehyde Finishing of Textiles[1]", 1981.

R. S. Perry, et al., Textile Chemists and Colorists, vol. 12, No. 12, pp. 311 to 316, "A Search for Potential Formaldehyde Acceptors", 1980.

*Primary Examiner*—Duc Truong
(74) *Attorney, Agent, or Firm*—Oblon, Spivak, McClelland, Maier & Neustadt, P.C.

(57) ABSTRACT

Organic compounds containing —$CH_2$—CHR—O— and/or —$CH_2$—CH(OH)— groupings (R=H, $C_1$–$C_4$-alkyl) produce, under the action of free radicals, small amounts of $C_1$–$C_2$-aldehydes, the content of which can be reduced to <1 ppm according to the novel process by adding compounds which can react with the aldehyde groups. The materials containing said groupings include many emulsifiers and protective colloids used in polymer chemistry, such as polyethylene glycols, polyvinyl alcohols or ethoxylation products of long-chain alcohols, phenols or amines. The process is of particular importance for the treatment of polymer dispersions which have been prepared by free-radical polymerization of monomers in the presence of such emulsifiers or protective colloids, and permits the preparation of aldehyde-free polymer dispersions and their use for sanitary and hygiene articles.

6 Claims, No Drawings

METHOD FOR REDUCING THE $C_1$-$C_2$-ALDEHYDE CONTENT FORMED FROM COMPOUNDS WITH -$CH_2$-CHR-O-OR-CH(OH)-GROUPS

The invention relates to a process for reducing a content of $C_1$–$C_2$-aldehydes formed, by the action of free radicals, from compounds containing —$CH_2$—CHR—O— or —$CH_2$—CH(OH)— groups.

It is known that, by virtue of their preparation, aqueous polymer dispersions or solutions may contain aldehyde derivative groups of monomers, crosslinkers or initiators or components thereof, e.g. N-methylol groups, esterified or etherified N-methylol groups, which can release certain amounts of $C_1$–$C_2$-aldehydes such as formaldehyde during storage or use or in the presence of acid. The corresponding dispersions or solutions, because of their content of free formaldehyde, are not used for a whole series of products, such as for sanitary products. It is known to add to such aldehyde-liberating products aldehyde scavengers which are able to bind the released aldehyde and in particular the formaldehyde and thus make the products more acceptable from a toxicological viewpoint (see e.g. EP-A 80635, EP-B 143175, EP-B 492378, EP-A 527411). It is also known (EP-A 492 378, EP-A 505959), to remove undesired amounts of formaldehyde or acetaldehyde by oxidation reactions.

It has now been found that it is not only aqueous polymer dispersions or solutions which contain aldehyde derivative groups of said type which are able to release $C_1$–$C_2$-aldehydes such as formaldehyde, but that, for example, aqueous polymer dispersions and solutions which, as emulsifiers or protective colloids, comprise compounds containing —$CH_2$—CHR—O— or —$CH_2$—CH(OH)— groups in the molecule (where R=H or $C_1$–$C_4$-alkyl radical) can also do this when they have been exposed to the action of a free radical, for example during their preparation. Compounds containing said groups are, for example, nonionogenic ethoxylated $C_6$–$C_{20}$-alcohols, $C_6$–$C_{20}$-amines or $C_4$–$C_{18}$-alkylphenols having a degree of ethoxylation of from 1 to 100 mols of ethylene oxide, polyethylene oxide having from 30 to 8000 mols of ethylene oxide in the molecule, block copolymers of polyethylene oxide and polypropylene oxide or polyvinyl alcohols, such as polyvinyl esters, the ester groups (e.g. acetate groups) of which have been from 50 to 98 mol % hydrolyzed. The ethoxylated alcohols, amines or alkylphenols can here also be in ionogenic, e.g. sulfated or phosphonated, form or in a salt form thereof. Other ethoxylated compounds containing polyether chains which are used in the preparation of polymer dispersions are, for example, ethoxylated hydroxyethylcelluloses, ethoxylated starch derivatives and ethoxylated monomers, such as ethoxylated 2-hydroxyethyl methacrylate. An overview of compounds having such structures which can be used in the polymerization is given, for example, in N. Schönfeld, Grenzflächenaktive Äthylenoxid-Addukte [Surface-active ethylene oxide adducts], Stuttgart 1976 and the supplementary volume from 1984, and Houben-Weyl, Vol. XIV/1, Stuttgart 1961, pages 190–208. These compounds containing —$CH_2$—CHR—O— and/or —$CH_2$—CH(OH)— groups, which have for decades been largely used industrially in the production of aqueous dispersions and solutions, have for a long time been regarded as wholly acceptable from a health point of view since the release of aldehyde therefrom has been masked by other aldehyde-liberating reactions. Although the literature states that high-energy rays, oxygen or peroxides are able to cause polyethylene oxide or polypropylene oxide chains to undergo a large number of reactions which can lead to degradation or, as a consequence of crosslinking reactions, also to an increase in the molecular weight (see, for example, Kaczmarek et al., Macromol. Symp. 84 (1994) 351–363; Janik, Abh. Akad. Wissenschaften DDR, Akademieverlag Berlin 1987, 551–555; Hidata et al. Yukagaku 1990, 39 (11), 963–966, C.A. 114: 8577m), the fact that such products, by the action of free radicals, can release traces of formaldehyde, acetaldehyde and/or glyoxal, with its consequences was not recognized.

In order to explain the degradation of such groups, it should be pointed out that in an ether chain H atoms in a $CH_x$—O— group can be readily abstracted by free radicals. Following H transfer, the free radical center is on the ethylene oxide chain, which can now undergo consecutive reactions, such as a monomer addition (emulsifier grafting), a combination with other free radicals or a degradation of the polyether chain. The latter leads to the formation of low molecular weight compounds. Whenever a —$CH_x$—O— compound encounters a free radical or a free-radical formation mechanism, a free-radical-induced degradation can take place, even in the case of ethylene glycol, ethylene glycol dimethyl ether or polyvinyl alcohol. The fact that during such a free-radical-induced degradation significant amounts of formaldehyde, acetaldehyde and/or glyoxal can be formed is a new finding.

Since formaldehyde, acetaldehyde and/or glyoxal are undesired even in low concentrations in products, can lead to discolorations of the products and, in particular, the presence of formaldehyde in products leads to toxicological reservations on the part of the processors, the novel aim was to reduce, in materials, dispersions or solutions which contain —$CH_2$—CHR—O— (R=H, $C_1$–$C_4$-alkyl) or —$CH_2$—CH(OH)— groups or compounds containing such groups, the content of small amounts of $C_1$–$C_2$-aldehydes, produced by the action of free radials, if at all possible to amounts below 1 ppm. This object is of particular importance in the field of the use of plastics dispersions, since, for example for the preparation of nonwovens for the sanitary and hygiene sector, regulations only permit the use of formaldehyde-free plastics dispersions in certain areas (cf. EP-A 143175, page 2, line 55 ff.).

We have found that this object can be achieved by a process for reducing a content of $C_1$–$C_2$-aldehydes formed, by the action of free radicals, from organic compounds containing —$CH_2$—CHR—O— or —$CH_2$—CH(OH)— groups (R=H, $C_1$–$C_4$-alkyl), in materials, dispersions or solutions which contain such groups or compounds with such groups, by adding compounds which react with the aldehyde. Preferred compounds which are added as compounds which react with aldehydes are nitrogen-containing compounds which bind aldehyde groups, such as urea or cyclic urea derivatives, or compounds which oxidize or reduce aldehyde groups. It was surprising that the content of $C_1$–$C_2$-aldehydes can be reduced by this method to amounts of 1 ppm and below, i.e. or GB 2086929. Water soluble copolymers containing amide groups are used in EP-A 527411 for reducing the formaldehyde content, and copolymers which contain copolymerized monomers with cyclic urea groups are also suitable for this purpose (EP-A 488605). Measures for reducing the formaldehyde content were and are also used widely in the field of particleboard processing (cf. GB 2086929, EP-A 341569) and, in particular, for removing formaldehyde from textiles treated (impregnated) with aqueous polymer dispersions or aqueous solutions of aminoplastic condensates (U.S. Pat. No. 3,590,100, U.S. Pat. No. 3,957,431). As well as urea and carbamates, cyclic compounds containing NH groups, such as compounds of the pyrrolidone type, and also benzimidazole compounds (U.S. Pat. No. 4,127,382) are also used as formaldehyde scavengers. The reduction in the amount of formaldehyde in aqueous dispersions can, according to EP-A 492378, also be effected by the action of peroxy compounds, such as hydrogen peroxide, organic peroxides, perborates, percarbonates, persulfates or perphosphates, although for the present intended process the use of aldehyde scavengers, i.e. of substances which bind the aldehyde, is preferred.

For a new objective and for other starting materials the measure to be carried out, of binding or chemically modifying $C_1$–$C_2$-aldehydes by means of additives, is in principle known per se, and can thus be carried out in accordance with the details in the prior art. The materials, dispersions or solutions to be treated according to the process always are or contain organic compounds containing —$CH_2$—CHR—O— (where R=H or $C_1$–$C_4$-alkyl) and/or —$CH_2$—CH(OH)— groups, from which, by the action of free radicals, such as in the case of a degradation of free radical initiators, small but unwanted amounts of $C_1$–$C_2$-aldehydes can form. Materials which contain such groups are, for example, polyvinyl alcohols, alkylene glycols having from 2 to 4 carbon atoms, polymers thereof and derivatives of such compounds, such as ethylene glycol dimethyl ether, or alkylene oxide and, in particular, ethylene oxide addition products with, for example, long-chain alcohols, phenols, amines etc., as are widely used as emulsifiers and protective colloids. Reference is made to examples of such compounds given above. The novel process is of particular importance in the treatment of dispersions and solutions comprising compounds containing said groups which act as emulsifiers and/or protective colloids in the preparation and/or use of polymer dispersions. For example, it is important for the treatment in accordance with the process of aqueous polymer dispersions or solutions which are prepared by free-radical polymerization and/or free-radical after polymerization of olefinically unsaturated monomers in the presence of organic compounds containing —$CH_2$—CHR—O— and/or —$CH_2$—CH(OH)— groups. Since the novel process is intended to reduce small amounts of $C_1$–$C_2$-aldehydes formed, by the action of free radicals, from —$CH_2$—CHR—O— or —$CH_2$—CH(OH)— groups to contents of below 1 ppm if at all possible, it is naturally unwise for the materials, dispersions or solutions to be treated to contain further compounds which are known to be able to release $C_1$–$C_2$-aldehydes. For example, the materials, dispersions or solutions to be treated according to the process should not contain monomers, monomer units, initiators and/or crosslinkers containing aldehyde derivative groups, such as N-methylol groups, nor etherified or esterified N-methylol groups, which, as is known, readily release aldehyde groups.

The examples below show that emulsifiers, protective colloids and block copolymers which contain ethylene oxide groups in bonded form are degraded in the presence of free radicals, forming $C_1$–$C_2$-aldehydes, in particular formaldehyde or acetaldehyde. The same is true of a free-radical action on monomer emulsions which comprise compounds containing '$CH_2$—CHR—O— or —$CH_2$—CH(OH)— groups (R=H, $C_1$–$C_4$-alkyl) in the emulsifier, protective colloid or monomer.

Formaldehyde is determined as follows:

Method 1: Determination of formaldehyde in the presence of other carbonyl compounds was carried out using a combination of HPLC separation of formaldehyde and chromatographic post column derivatization using acetylacetone, the lutidine derivative forming being quantified against an external calibration. The method is described inter alia by H. Engelhardt and R. Klinckner in the article "Determination of Free Formaldehyde in the Presence of Donators in Cosmetics by HPLC and Post Column Derivation" in Chromatographia Vol.20, No.9 (1985) 559–565 and by U. Schäfer-Lüderssen and M. Mauβ in the article "Determination of Free Formaldehyde in Nonwovens in the Presence of Glyoxalic Acid and Aldehydes" in Chromatographia Vol.29, No.1/2 (1990) 21–23.

Method 2: A sample of the substance to be investigated is reacted with 2,4-dinitrophenylhydrazine, and the obtained hydrazones are separated by HPLC on an RP phase (Licrospher 100 RP 18.5 µm, (125×4 mm), $H_2O$/acetonitrile eluent, flow rate 1.0 ml/min. detection at 370 nm). The product peak was identified using reference substances.

Unless stated otherwise, parts and percentages given in the examples below are by weight. "(xEO)" means that x molecules of ethylene oxide have been bonded to one molecule of the compound in question by ethoxylation.

In order to determine the foam, nitrogen was blown through a graduated glass cylinder with glass frit (internal diameter 35 mm, porosity of the frit: 2) via a pressure-reducing valve at a pressure of about 0.2 bar and at 3.5 liters/minute. After 25 g of polymer dispersion had been poured in, the development of foam was monitored in terms of volume over the course of time, and the 6 minute value was recorded.

The light transparency (LT net value) was determined by comparing the light transparency of a 0.01% by weight strength sample of the polymer dispersion at a path length of 25 mm with that of pure water.

The residual monomer content was determined by gas chromatography. The solids content (SC) in % by weight were determined gravimetrically after drying.

EXAMPLE 1

Formaldehyde from Ethoxylated Emulsifiers a. Emulsifiers: in each case 3.2% strength stock solutions were prepared using the following emulsifiers:

Emulsifier E1: mixture of the sodium salt of sulfated p-octylphenol ethoxylate (25 EO) and nonsulfated p-octylphenol ethoxylate (25 EO) in the mixing ratio 1:1.

Emulsifier E2: sodium salt of sulfated $C_{12}$-fatty alcohol ethoxylate (3 EO). Had already been preserved against bacterial attack using formaldehyde.

Emulsifier E3: Sodium salt of sulfated $C_{12}$-fatty alcohol-ethoxylate (50 EO).

Emulsifier E4: polyethylene glycol (molecular weight 9000)

Emulsifier E5: sodium lauryl sulfate (0 EO), Comparative Experiment b. Treatment with sodium persulfate (NaPS)

200 g of each of the emulsifier solutions E1 to E5 were heated to 85° C. under nitrogen, and 101 g of a solution of 8.1 g of sodium persulfate in 600 g of water were added continuously over the course of 2 hours. The mixtures were held for a further hour at 85° C. The formaldehyde contents in the resulting emulsifier solutions were determined. The results are shown in Table 1.

c.Treatment with hydrogen peroxide/ascorbic acid ($H_2O_2$/Asc) Under nitrogen, 200 g of each of emulsifier solutions E1 to E5 were treated with 1.2 g of hydrogen peroxide (30%) and heated to 60° C. Over the course of 2 hours, a solution of 2.16 g of ascorbic acid and 100 mg of iron(II) sulfate heptahydrate in 100 g of water was added continuously to each, and then the mixtures were stirred for 1 hour at 60° C. The formaldehyde contents in the resulting mixtures were determined. The results are given in Table 1.

d. Treatment with azo initiator V50 (AZO)

Under nitrogen, 200 g of each of the emulsifier solutions E1 to E5 were heated to 85° C., and over the course of 2 hours, 100 g of a solution of 9.24 g of 2,2'-azobis(2-amidinopropane) dihydrochloride (V50 from Wako Chem.) in 600 g of water were continuously added to each. The mixtures were then held at 85° C. for 1 hour. The formaldehyde contents in the resulting mixtures were determined. The results are given in Table 1.

TABLE 1

Formaldehyde content (ppm) of initiator-treated emulsifier

| Emulsifier | nEO * | untreated | NaPS | $H_2O_2$/Asc. | AZO |
|---|---|---|---|---|---|
| E1 | 25 | <1 | 81 | 73 | 9 |
| E2 | 3 | 16 ** | 39 | 12 | 19 |
| E3 | 50 | <1 | 71 | 68 | 26 |
| E4 | 200 | 1 | 43 | 74 | 27 |
| E5 | 0 | <1 | 1 | 2 | 3 |

\* gives the approximate number of mols of EO per mole of emulsifier
\*\* emulsifier E2 contains some formaldehyde as preservative

EXAMPLE 2

Formaldehyde from Model Compound Solutions a. Solutions of model compounds S1 to S4

The following solutions of model compounds were prepared:

Solution S1: 3% strength solution of ethylene glycol

Solution S2: 3% strength solution of ethylene glycol dimethyl ether

Solution S3: 10% strength solution of polyvinyl alcohol (Moviol 3-83)

Solution S4: 0.1% strength solution of n-butyl acrylate.

b. Treatment of solutions S1–S4 with sodium persulfate

Solutions S1 to S4 were treated as stated in Example 1b. The formaldehyde contents in the resulting mixtures were determined, and in the case of S4 the residual monomer content was determined. The results are given in Table 2.

c. Treatment of solutions S1–S4 with hydrogen peroxide/ascorbic acid ($H_2O_2$/Asc.)

Solutions S1–S4 were treated as stated in Example 1c. The formaldehyde contents in the resulting mixtures were determined, and in the case of S4 the residual monomer content was determined. The results are given in Table 2.

d. Treatment of solutions S1–S4 with tert-butyl hydroperoxide and ascorbic acid (tBHP/Asc.)

At 60° C., 1.0 g of tert-butyl hydroperoxide (70% strength) and 200 g of a solution of 2.16 g of ascorbic acid and 10 mg of iron(II) sulfate heptahydrate in 600 g of water were added to 200 g of each of solutions S1 to S4, and then the mixtures were stirred in each case for 1 hour. The formaldehyde contents in the resulting mixtures were determined, and in the case of S4 the residual monomer content was determined. The results are given in Table 2.

e. Treatment of a n-butyl acrylate solution 400 g of the n-butyl acrylate solution were treated according to the treatments of solutions S1 to S3, and in each case the residual monomer content was determined by gas chromatography. It was always <10 ppm, thus proving that the experiments were carried out under polymerization conditions.

TABLE 2

Formalde content in the case of initiator-treated model compounds

| Model compound | NaPS | $H_2O_2$/Asc. | tBHP/Asc. |
|---|---|---|---|
| S1-ethylene glycol | 37 | 22 | 7 |
| S2-ethylene glycol-dimethyl ether | 106 | 121 | 25 |
| S3-polyvinyl-alcohol | 3 | 9 | 10 |
| S4-n-butyl acrylate | <10* | <10* | <10* |

*Residual monomer content of n-butyl acrylate

EXAMPLE 3

Addition of Varying Amounts of Hydrogen Peroxide to an Ethoxylated Emulsifier 60 g of differently concentrated solutions of hydrogen peroxide in water were added in each case to 200 g of a 3% strength solution of the sodium salt of a $C_{12}$-fatty alcohol polyethylene oxide sulfate (ca. 30 EO) as emulsifier, and the mixture was heated to 60° C. Ascorbic acid (2.5 times the amount by weight of hydrogen peroxide) and 5 drops of a 1% strength iron(II) sulfate solution were diluted with water to 60 g of solution and added to the emulsifier solution over the course of 2 hours. After cooling, the resultant amounts of formaldehyde, acetaldehyde and glyoxal (in ppm) in each of the mixtures were determined by method 2. The results are given in Table 3.

TABLE 3

Aldehyde content as a function of the amount of hydrogen peroxide

| Ex. | $H_2O_2$ to emulsifier mixing ratio | Formaldehyde ppm | Acetaldehyde ppm | Glyoxal ppm |
|---|---|---|---|---|
| 3a | 0 | 1 | <0.5 | <0.5 |
| 3b | 0.1 | 3 | 0.5 | 0.5 |
| 3c | 0.2 | 6 | 3 | 4 |
| 3d | 0.3 | 5 | 0,8 | 2 |
| 3e | 0.5 | 11 | 2 | 9 |
| 3f | 1.0 | 21 | 5 | 15 |
| 3g | 1.0* | 61(113) | 2(5) | 32(4) |
| 3h | 5.0 | 77 | 102 | 106 |
| 3i | 10 | 22 | 116 | 100 |
| 3k | 1.0** | 6 | 2 | 3 |

*In the case of experiment 3g, the formaldehyde value was increased using 4 drops of formaldehyde solution prior to the reaction. The numbers in brackets give the aldehyde values prior to the addition of the reducing agent. The decrease in the formaldehyde value can be attributed to an approximately equal extent to the dilution and the oxidation.
**In the case of experiment 3k, the emulsifier solution was replaced by pure water. The aldehydes are not formed from the ascorbic acid.

EXAMPLE 4

Comparison of Emulsifier with Block Copolymer

In each case 200 ml of 3% strength aqueous solutions of the sodium salt of a $C_{12}$-fatty alcohol polyethylene oxide sulfate (ca. 30 EO) (EMU-4) and a polystyrene-polyethylene oxide block copolymer having an average degree of polymerization of 10 or 70 (SE 1030 from Th. Goldschmidt) were treated with an aqueous solution of 8.1 g of sodium persulfate in 600 g of water at 85° C. over the course of 2 hours. The mixture was then stirred for 1 hour and cooled.

The content of formaldehyde and acetaldehyde was determined by Method 2. The results are given in Table 4.

TABLE 4

Treatment of emulsifier and block copolymer

| Emulsifier | Treatment with | Formaldehyde ppm | Acetaldehyde ppm |
|---|---|---|---|
| EMU-4 | untreated | <5 | <5 |
| PS-PEO-Block | untreated | <5 | <5 |
| EMU-4 | persulfate | 150 | 500 |
| PS-PEO-Block | persulfate | 50 | 100 |

EXAMPLE 5

Reduction in Glyoxal 50 ml of a 1 molar aqueous solution of glyoxal were in each case mixed with 50 ml of differently concentrated solutions of urea and ethyleneurea (0.5 M, 1 M, 2 M), which are dissolved in 5% strength potassium hydrogensulfate solution, and left to stand for 24 hours at 25° C. The content of free glyoxal in the mixture was then determined by method 2. The determination was carried out by separating off glyoxal by HPLC on a RP column with subsequent derivatization using acetylacetone. The resultant lutidine derivative was quantified using UV detection by the method of the external standard. Table 5 gives the recovered percentage amount of glyoxal used.

TABLE 5

Glyoxal determination

| Addition of | % amount of recovered glyoxal |
|---|---|
| Water | 100 |
| 0.5 M urea | 87 |
| 1 M urea | 80 |
| 2 M urea | 61 |
| 0.5 M ethylene urea | 100 |
| 1 M ethylene urea | 92 |
| 2 M ethylene urea | 83 |

EXAMPLE 6

A monomer emulsion ME6 was prepared from 6.29 kg of water, 0.90 kg of a sodium salt of sulfated $C_{12}$-fatty alcohol (50 EO), 13.0 kg of ethyl acrylate and 0.50 kg of acylamidoglycolic acid.

An initial charge of 7.17 kg of water and 54 g of hydrogen peroxide (50%) was heated to 60° C. under nitrogen, and 400 g of the monomer emulsion ME6 and 100 g of a solution of 27 g of ascorbic acid and 0.15 g of iron(II) sulfate in 2 kg of water were added thereto, and the mixture was stirred for 15 minutes. The remaining monomer emulsion ME6 was metered in over the course of 120 minutes, and the remaining reducing agent solution was continuously metered in over the course of 135 minutes. After cooling, 20 g of a 10% strength aqueous solution of tert-butyl hydroperoxide and 13 g of a 10% strength solution of ascorbic acid were added to the mixture. After a sample had been taken, a solution of 13.5 g of ethyleneurea in 54 g of water was added, and the mixture stirred for 1 hour at 25° C. A low-viscosity dispersion (16 mPas at 480/s) with a solids content of 44.2% and a light transparency of 68% was obtained. The coagulate content was 0.13%. The formaldehyde content was 11 ppm prior to the addition of ethyleneurea, and <1 ppm following the addition.

EXAMPLE 7

Example 6 was repeated, but using 67.5 g of urea instead of the ethyleneurea. The amount of formaldehyde decreased from 20 ppm to <1 ppm.

EXAMPLE 8

4 Monomer mixtures each comprising 650 g of water, 720 g of n-butyl acrylate, 456 g of methyl methacrylate and 24 g of acrylic acid were converted into 4 monomer emulsions ME-8A to ME-8D by adding the emulsifiers A to F given in Table 6:

Emulsifier A: Sodium salt of a sulfated $C_{12}$-fatty alcohol ethoxylate (50 EO) 30% strength.

Emulsifier B: $C_{16}$–$C_{18}$-fatty alcohol ethoxylate (30 EO) 20% strength.

Emulsifier C: Sodium salt of sulfated p-octylphenol ethoxylate (25EO) 35% strength.

Emulsifier D: p-Octylphenol ethoxylate (25 EO) 20% strength.

Emulsifier E: Polyethylene oxide molecular weight 200 g/mol

Emulsifier F: Sodium lauryl sulfate 15% strength.

In each case 880 g of water were heated to 85° C. under nitrogen, and in each case 38 g of one of the monomer emulsions EM-8A to ME-8D and 12 g of an initiator solution of 8 g of sodium persulfate in 234 g of water (initiator solution I8) were added, and the mixture was stirred for 15 minutes. In each case the remainder of monomer emulsions ME-8A to ME-8D was metered in to the mixtures held at 85° C. over the course of 120 minutes, and the remainder of the initiator solution I8 was continuously metered in, and then each of the mixtures was stirred for a further 1 hour. After cooling, 12 g of tert-butyl peroxide and 12 g of ascorbic acid (each in the form of 10% strength aqueous solutions) were added to each mixture. In each case the formaldehyde contents in the resulting 4 coagulate-free polymer dispersions were determined by Method 1, as were the solids contents, the light transparencies (LT), the pH and, as given above, the foam formation. The results in Table 6 show that the comparative experiment d with sodium lauryl sulfate releases significantly less formaldehyde and leads to enhanced foam formation.

TABLE 6

Formation of formaldehyde and foam for a variety of emulsifiers

| | Experiment | | | |
|---|---|---|---|---|
| | a | b | c | d |
| Emulsifier: amount/type | 40 g A + 30 g B | 52 g C + 60 g D | 3.6 g E + 56 g F | 80 g F (comp.) |
| Solids content % | 39.4 | 39.6 | 39.4 | 39.7 |
| pH | 2.0 | 1.9 | 1.8 | 1.9 |
| LT % | 46 | 33 | 28 | 38 |
| Foam formation | 170 | 130 | 200 | 650 |
| Formaldehyde ppm | 21 | 8 | 9 | 4 |

We claim:

1. A process comprising free-radical polymerizing olefinically unsaturated monomers in the presence of organic compounds having —$CH_2$—CHR—O— and/or —$CH_2$—CH(OH)— groups, wherein R is H or $C_1$–$C_4$ alkyl, to form a polymer dispersion or solution, and scavenging $C_1$–$C_2$ aldehydes formed by the action of free radicals on said organic compounds having said groups by adding nitrogen-containing compounds which bind aldehyde groups.

2. The process as claimed in claim 1, wherein said nitrogen-containing compounds are urea and/or urea derivatives.

3. The process as claimed in claim 1, wherein said polymer dispersion or solution comprises organic compounds selected from the group consisting of organic compounds having —$CH_2$—CHR—O—groups, $C_1$–$C_4$-alkylene glycols, poly-$C_1$–$C_4$-alkylene glycols or derivatives thereof.

4. The process as claimed in claim 1, wherein said polymer dispersion or solution comprises organic compounds selected from the group consisting of organic compounds having —$CH_2$—CH(OH)— groups and polyvinyl alcohols.

5. The process as claimed in claim 1, wherein said organic compounds having —$CH_2$—CHR—O— and/or —$CH_2$—CH(OH)— groups are emulsifiers and/or protective colloids.

6. A process as claimed in claim 1, wherein said polymer dispersion or solution does not contain monomers, monomer units, initiators and/or crosslinkers containing N-methylol groups and/or ethers or esters of such groups.

* * * * *

UNITED STATES PATENT AND TRADEMARK OFFICE
CERTIFICATE OF CORRECTION

PATENT NO.    : 6,380,353 B1                                          Page 1 of 1
DATED         : April 30, 2002
INVENTOR(S)   : Rupaner et al.

It is certified that error appears in the above-identified patent and that said Letters Patent is hereby corrected as shown below:

<u>Title page,</u>
Item [54], the Title should read:

-- [54]  METHOD FOR REDUCING THE C1-C2-ALDEHYDE CONTENT FORMED FROM COMPOUNDS WITH-CH2-CHR-O-OR-CH2-CH(OH)-GROUPS --

Signed and Sealed this

Twenty-second Day of October, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,380,353 B1
DATED : April 30, 2002
INVENTOR(S) : Rupaner et al.

It is certified that error appears in the above-identified patent and that said Letters Patent is hereby corrected as shown below:

<u>Title page, Item [54] and Column 1, lines 1-4,</u>
Title, should read:

-- [54] METHOD FOR REDUCING THE $C_1$-$C_2$-ALDEHYDE CONTENT FORMED FROM COMPOUNDS WITH -$CH_2$-CHR-O- OR -$CH_2$-CH(OH)-GROUPS --

Signed and Sealed this

Twenty-ninth Day of July, 2003

JAMES E. ROGAN
*Director of the United States Patent and Trademark Office*